US010894061B2

(12) United States Patent
Blazar et al.

(10) Patent No.: US 10,894,061 B2
(45) Date of Patent: Jan. 19, 2021

(54) THERAPEUTIC METHODS INVOLVING MODULATING INFLAMMASOME ACTIVATION OF MYELOID-DERIVED SUPPRESSOR CELLS

(71) Applicants: Regents of the University of Minnesota, Minneapolis, MN (US); St. Jude Children's Research Hospital, Inc., Memphis, TN (US); Albert-Ludwig Universität Freiburg, Freiburg (DE); The University of North Carolina at Chapel Hill, Chapel Hill, NC (US)

(72) Inventors: Bruce R. Blazar, Golden Valley, MN (US); Brent Koehn, Elk River, MN (US); Peter J. Murray, Memphis, TN (US); Jenny P. Y. Ting, Chapel Hill, NC (US); Robert Zeiser, Freiburg (DE); Jeff S. Miller, Little Canada, MN (US)

(73) Assignees: Regents of the University of Minnesota, Minneapolis, MN (US); The University of North Carolina at Chapel Hill, Chapel Hill, NC (US); Albert-Ludwigs-Universität Freiburg; St. Jude Children's Research Hospital, Inc., Memphis, TN (US)

( * ) Notice: Subject to any disclaimer, the term of this patent is extended or adjusted under 35 U.S.C. 154(b) by 46 days.

(21) Appl. No.: 15/747,902

(22) PCT Filed: Aug. 5, 2016

(86) PCT No.: PCT/US2016/045739
§ 371 (c)(1),
(2) Date: Jan. 26, 2018

(87) PCT Pub. No.: WO2017/024213
PCT Pub. Date: Feb. 9, 2017

(65) Prior Publication Data
US 2018/0214483 A1    Aug. 2, 2018

Related U.S. Application Data

(60) Provisional application No. 62/201,990, filed on Aug. 6, 2015.

(51) Int. Cl.
| | | |
|---|---|---|
| *A01N 63/00* | (2020.01) |
| *A61K 48/00* | (2006.01) |
| *A61K 35/15* | (2015.01) |
| *C12N 5/0787* | (2010.01) |
| *C12N 5/078* | (2010.01) |
| *A61P 37/06* | (2006.01) |
| *A61K 39/00* | (2006.01) |
| *A61K 45/06* | (2006.01) |
| *C12N 5/0786* | (2010.01) |
| *A61K 35/12* | (2015.01) |

(52) U.S. Cl.
CPC ............ *A61K 35/15* (2013.01); *A61K 39/001* (2013.01); *A61K 45/06* (2013.01); *A61P 37/06* (2018.01); *C12N 5/0642* (2013.01); *C12N 5/0645* (2013.01); *C12N 5/0648* (2013.01); A61K 2035/122 (2013.01); A61K 2035/124 (2013.01); A61K 2039/515 (2013.01); A61K 2039/545 (2013.01); A61K 2039/577 (2013.01); C12N 2501/22 (2013.01); C12N 2501/2313 (2013.01); C12N 2501/24 (2013.01)

(58) Field of Classification Search
None
See application file for complete search history.

(56) References Cited

U.S. PATENT DOCUMENTS

2008/0038238 A1    2/2008 Huberman et al.

FOREIGN PATENT DOCUMENTS

| WO | WO 2010/062990 | 6/2010 | |
| WO | WO-2011087795 A2 * | 7/2011 | ........... A61K 31/137 |

OTHER PUBLICATIONS

Sheng et al., 2013, Med. Res. Rev. vol. 33: 1119-1173.*
Rezvani et al., 2012, Exp. Opin. PHarm. vol. 13: 1737-1750.*
Goncalves et al., 2017, Einsten, vol. 15: 369-75.*
Lino et al., Drug Delivery, vol. 25: 1234-1257.*
Latz et al., 2013, Nat. Rev. Immunol. vol. 13: 1-31.*
Li et al., 2018, Mol. Med. Report. vol. 18: 4399-4409.*
Barker et al., "Cross-regulation between the IL-1β/IL-18 processing inflammasome and other inflammatory cytokines," Curr. Opin. Immunol., Oct. 2011, 23(5):591-597.
Blazar et al., "Advances in graft-versus-host disease biology and therapy," Nat. Rev. Immunol., May 2012, 12(6):443-458.
Borge et al., "Ability of early acting cytokines to directly promote survival and suppress apoptosis of human primitive CD34+CD38− bone marrow cells with multilineage potential at the single-cell level: key role of thrombopoietin," Blood, Sep. 1997, 90(6):2282-92.
Boros et al., "Myeloid-derived suppressor cells: natural regulators for transplant tolerance," Hum. Immunol., Nov. 2010, 71(11):1061-66.

(Continued)

*Primary Examiner* — Amy E Juedes
(74) *Attorney, Agent, or Firm* — Fish & Richardson P.C.

(57) ABSTRACT

In one aspect, a method of treating a subject having or at risk of having graft-versus-host disease (GvHD) generally includes administering to the subject a plurality of myeloid-derived suppressor cells (MDSCs) effective to ameliorate at least one symptom or clinical sign of graft-versus-host disease compared to a suitable control subject. In another aspect, a method of treating a tumor in a subject generally includes administering to the subject an anti-tumor therapy and co-administering to the subject an inflammasome inciting agent in an amount effective to increase inflammasome activation of MDSCs sufficiently to reduce suppressor function of the MDSCs.

30 Claims, 10 Drawing Sheets

(56) References Cited

OTHER PUBLICATIONS

Bruchard et al., "Chemotherapy-triggered cathepsin B release in myeloid-derived suppressor cells activates the Nlrp3 inflammasome and promotes tumor growth," Nat. Med., Dec. 2012, 19(1):57-64.
Brunstein et al., "Infusion of ex vivo expanded T regulatory cells in adults transplanted with umbilical cord blood: safety profile and detection kinetics," Blood, Jan. 2011, 117(3):1061-1070.
Cheng et al., "Inhibition of dendritic cell differentiation and accumulation of myeloid-derived suppressor cells in cancer is regulated by S100A9 protein," J. Exp. Med., Sep. 2008, 205(10):2235-49.
Chou et al., "Hepatic stellate cells regulate immune response by way of induction of myeloid suppressor cells in mice," Hepatology, Mar. 2011, 53(3):1007-1019.
Coll et al., "A small-molecule inhibitor of the NLRP3 inflammasome for the treatment of inflammatory diseases," Nat. Med., Mar. 2015, 21(3):248-255.
Cooke et al., "LPS antagonism reduces graft-versus-host disease and preserves graft-versus-leukemia activity after experimental bone marrow transplantation," J. Clin. Invest., Jun. 2001, 107(12):1581-1589.
Deknuydt et al., "IL-1beta and IL-2 convert human Treg into T(H)17 cells," Clin. Immunol., May 2009, 131(2):298-307.
Dinarello, "Immunological and inflammatory functions of the interleukin-1 family," Annu. Rev. Immunol., Apr. 2009, 27:519-550.
Gabrilovich and Nagaraj, "Myeloid-derived suppressor cells as regulators of the immune system," Nat. Rev. Immunol., Mar. 2009, 9(3):162-174.
Galli et al., "Phenotypic and functional plasticity of cells of innate immunity: macrophages, mast cells and neutrophils," Nat. Immunol., Oct. 2011, 12(11):1035-1044.
Greten et al., "Myeloid derived suppressor cells in human diseases," Int. Immunopharmacol., Jul. 2011, 11(7):802-807.
Haverkamp et al., "Myeloid-Derived Suppressor Activity Is Mediated by Monocytic Lineages Maintained by Continuous Inhibition of Extrinsic and Intrinsic Death Pathways," Immunity., Dec. 2014, 41(6):947-959.
Highfill et al., "Bone marrow myeloid-derived suppressor cells (MDSCs) inhibit graft-versus-host disease (GVHD) via an arginase-1-dependent mechanism that is up-regulated by interleukin-13," Blood, Dec. 2010, 116(25):5738-5747.
Hill et al., "Total Body Irradiation and Acute Graft-Versus-Host Disease: The Role of Gastrointestinal Damage and Inflammatory Cytokines," Blood, Oct. 1997, 90(8):3204-3213.
Hippen et al., "Umbilical cord blood regulatory T-cell expansion and functional effects of tumor necrosis factor receptor family members OX40 and 4-1BB expressed on artificial antigen-presenting cells," Blood, Oct. 2008, 112(7):2847-2857.
Holtan et al, "Acute graft-versus-host disease: a bench-to-bedside update," Blood, Jul. 2014, 124(3):363-373.
International Preliminary Report on Patentability in International Application No. PCT/US2016/045739 dated Feb. 21, 2018, 10 pages.
Jankovic et al., "The Nlrp3 inflammasome regulates acute graft-versushost disease," J. Exp. Med., Sep. 2013, 210(10):1899-1910.
Lechner et al., "Characterization of cytokine-induced myeloid-derived suppressor cells from normal human peripheral blood mononuclear cells," J. Immunol., Aug. 2010, 185(4):2273-2284.
Li et al., "Graft-versus-host disease is independent of innate signaling pathways triggered by pathogens in host hematopoietic cells," J. Immunol., Jan. 2011, 186(1):230-241.
Li et al., "Myeloid-derived suppressor cells as a potential therapy for experimental autoimmune myasthenia gravis," J. Immunol., Sep. 2014, 193(5):2127-2134.
Lu et al., "Unified Polymerization Mechanism for the Assembly of ASCDependent Inflammasomes," Cell, Mar. 2014, 156(6):1193-1206.
Mariathasan et al., "Differential activation of the inflammasome by caspase-1 adaptors ASC and Ipaf," Nature, Jul. 2004, 430(6996):213-218.
Marigo et al., "Tumor-induced tolerance and immune suppression by myeloid derived suppressor cells," Immunol. Rev., Apr. 2008, 222:162-179.
Markey et al., "The biology of graft-versus-host disease: experimental systems instructing clinical practice," Blood, Jul. 2014, 124(3):354-362.
Martinon et al., "The inflammasomes: guardians of the body," Annu. Rev. Immunol., Apr. 2009, 27:229-265.
McCarthy et al., "Inhibition of interleukin-1 by an interleukin-1 receptor antagonist prevents graft-versus-host disease," Blood, Oct. 1991, 78(8):1915-1918.
Messmann et al., "In vitro-generated MDSCs prevent murine GVHD by inducing type 2 T cells without disabling antitumor cytotoxicity" Blood, Aug. 2015, 126(9):1138-1148.
Ostrand-Rosenberg and Sinha, "Myeloid-derived suppressor cells: linking inflammation and cancer," J. Immunol., Apr. 2009, 182(8):4499-4506.
O'Sullivan et al., "IL-1 beta breaks tolerance through expansion of CD25+ effector T cells," J. Immunol., Jun. 2006, 176(12):7278-7287.
Peranzoni et al., "Myeloid-derived suppressor cell heterogeneity and subset definition," Curr. Opin. Immunol., Apr. 2010, 22(2):238-244.
Reddy et al., "Pretreatment of donors with interleukin-18 attenuates acute graft-versus-host disease via STAT6 and preserves graft-versus-leukemia effects," Blood, Apr. 2003, 101(7):2877-2885.
Reddy et al., "Role of interleukin-18 in acute graft-vs-host disease," J. Lab. Clin. Med., Jun. 2003, 141(6):365-371.
Reese et al., "Chitin induces accumulation in tissue of innate immune cells associated with allergy," Nature, May 2007, 447(7140):92-96.
Schroder and Tschopp, "The inflammasomes," Cell, Mar. 2010, 140(6):821-832.
Sica and Bronte, "Altered macrophage differentiation and immune dysfunction in tumor development," J. Clin. Invest., May 2007, 117(5):1155-66.
Socié and Ritz, "Current issues in chronic graft-versus-host disease," Blood, Jul. 2014, 124(3):374-384.
Stout and Suttles, "Functional plasticity of macrophages: reversible adaptation to changing microenvironments," J. Leukoc. Biol., Sep. 2004, 76(3):509-513.
Taylor et al., "TLR agonists regulate alloresponses and uncover a critical role for donor APCs in allogeneic bone marrow rejection," Blood, Oct. 2008, 112(8):3508-3516.
Wang et al., "Dynamic Change and Impact of Myeloid-Derived Suppressor Cells in Allogeneic Bone Marrow Transplantation in Mice," Biol. Blood Marrow Transplant., May 2013, 19(5):692-702.
Welniak et al., "Immunobiology of allogeneic hematopoietic stem cell transplantation," Annu. Rev. of Immunol., Apr. 2007, 25(1):139-170.
Wilhelm et al., "Graft-versus-host disease is enhanced by extracellular ATP activating P2X7R," Nat. Med., Dec. 2010, 16(12):1434-1438.
Youm et al., "The ketone metabolite [beta]-hydroxybutyrate blocks NLRP3 inflammasome-mediated inflammatory disease," Nat. Med., Mar. 2015, 21(3):263-269.
Youn and Gabrilovich, "The biology of myeloid-derived suppressor cells: the blessing and the curse of morphological and functional heterogeneity," Eur. J. Immunol., Nov. 2010, 40(11):2969-2975.
Zhou et al., "Development and function of myeloid-derived suppressor cells generated from mouse embryonic and hematopoietic stem cells," Stem Cells., Mar. 2010, 28(3):620-632.

* cited by examiner

THERAPEUTIC METHODS INVOLVING MODULATING INFLAMMASOME ACTIVATION OF MYELOID-DERIVED SUPPRESSOR CELLS

CROSS-REFERENCE TO RELATED APPLICATION

This application is the § 371 U.S. National Stage of International Application No. PCT/US2016/045793, filed Aug. 5, 2016, which claims priority to U.S. Provisional Patent Application No. 62/201,990, filed Aug. 6, 2015, each of which is incorporated herein by reference in its entirety.

GOVERNMENT FUNDING

This invention was made with government support under HL056067, AI034495, HL118979, CA156330, and AI067798, awarded by the National Institutes of Health. The government has certain rights in the invention.

SUMMARY

This disclosure describes, in one aspect, a method of treating a subject having or at risk of having graft-versus-host disease (GvHD). Generally, the method includes administering to the subject a plurality of myeloid-derived suppressor cells (MDSCs) effective to ameliorate at least one symptom or clinical sign of graft-versus-host disease compared to a suitable control subject.

In some embodiments, the method includes a plurality of serial administrations of MDSCs as previously-administered MDSCs experience inflammasome activation.

In some embodiments, at least a portion of the plurality of MDSCs comprises a genetic modification causing the MDSC to resist inflammasome activation.

In some embodiments, the method includes co-administering to the subject an agent that inhibits inflammasome activation.

In another aspect, this disclosure describes a method of treating a tumor in a subject. Generally, the method includes administering to the subject an anti-tumor therapy and co-administering to the subject an inflammasome inciting agent in an amount effective to increase inflammasome activation of MDSCs sufficiently to reduce suppressor function of the MDSCs.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
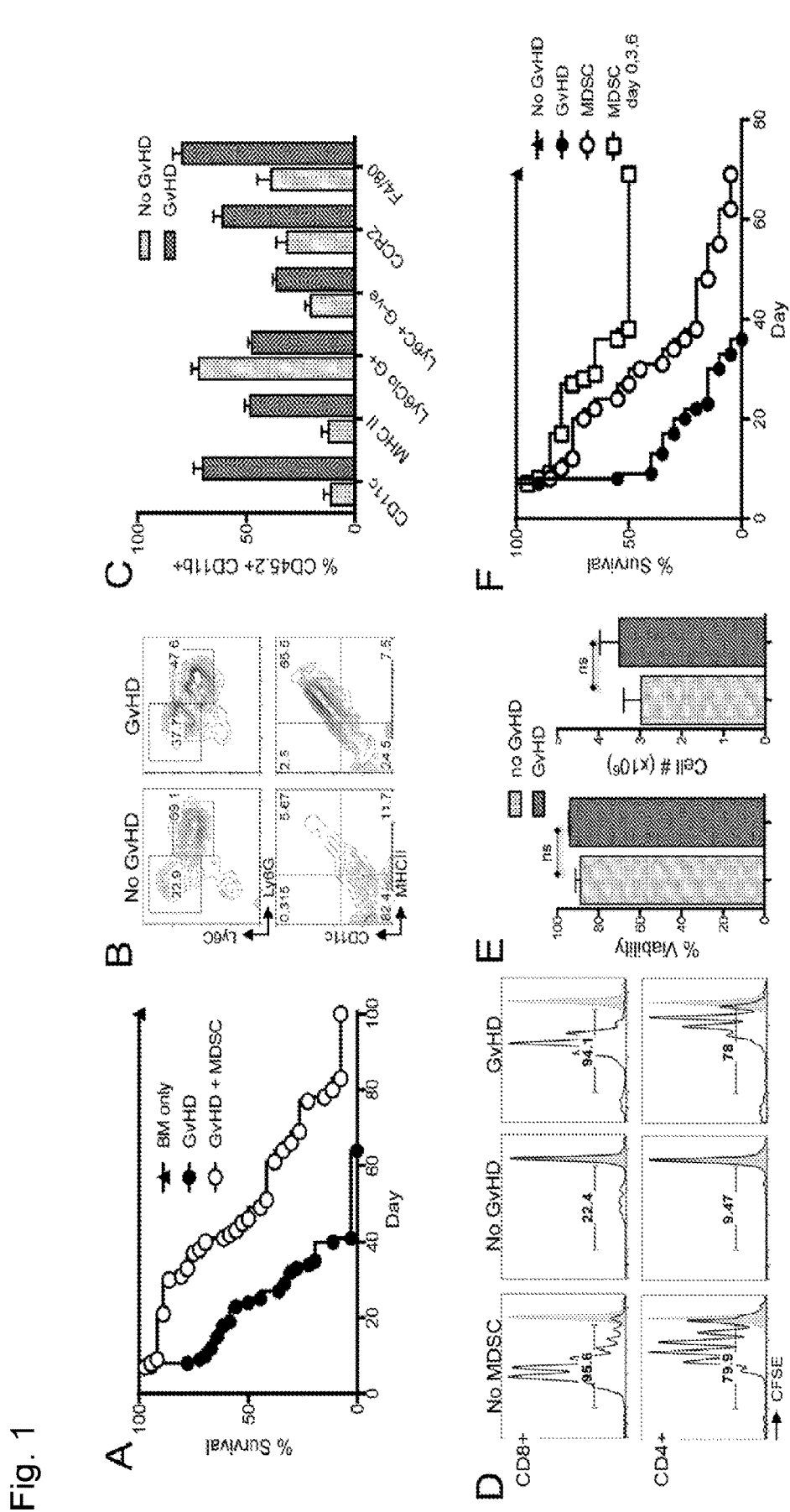
FIG. 1. Bone marrow derived MDSC-IL13 enhance GvHD survival, but suppression is compromised after five days in vivo. (A) Lethally irradiated BALB/c recipients were given $1 \times 10^7$ C57B1/6 bone marrow (BM only), or bone marrow plus $2 \times 10^6$ CD25-depleted T cells (GvHD) or bone marrow, T cells and $6 \times 10^6$ MDSC-IL13 (GvHD+MDSC-IL13) as indicated. Kaplan-Meier survival curve represents four pooled and independent experiments (n=40 animals/group). GvHD vs. GvHD+MDSC, p<0.0001. (B-C) Surface expression of congenic (CD45.2$^+$) MDSC-13 recovered from spleens five days after transfer to irradiated animals receiving bone marrow only (no GvHD) or bone marrow plus T cells (GvHD). Data represents three replicates per group with p<0.001 for all markers shown. (D) Representative histograms indicating responding T cell proliferation as denoted by CFSE dilution. Purified MDSC-13 from pooled spleens five days after transplant were plated at $5 \times 10^5$/mL with an equal number of CFSE-labeled responder T cells, 0.25 µg/ml anti-CD3ε mAb and $2.5 \times 10^5$/ml irradiated T cell depleted splenocytes in specially formulated 150 µM L-Arginine RPMI media. Shaded histogram indicates proliferation of unstimulated controls. Data are representative of three samples per group and a total of three independent experiments. (E) Summary data of recovered MDSC showing viability and total cell numbers recovered, gated CD11b$^+$ CD45.2$^+$. Data represents three samples per group and is representative of three independent experiments. (F) Lethally irradiated Balb/c recipients transplanted as above, or given three consecutive infusions of MDSC-13 as indicated on day 0, day 3, and day 6. All mice receiving MDSC demonstrated increased survival vs GvHD, p<0.001. MDSC vs MDSC day 0, day 3, and day 6 p<0.0001. Survival curve represents 20 animals per group from two independent experiments, and is representative of an additional experiment giving multiple infusions on day 0, day 7, and day 14.

This disclosure describes, in one aspect, a method of improving the use of myeloid-derived suppressor cells (MDSCs) for inhibiting graft-versus-host disease (GvHD). Generally, the methods involve combining the use of MDSCs with at least one approach for limiting in vivo MDSC inflammasome activation.

Myeloid-derived suppressor cells (MDSC) are a naturally-occurring immune regulatory population involved in inhibiting ongoing inflammatory responses. In vitro MDSC generation from bone marrow can enhance survival in an acute model of lethal graft-versus-host disease (GvHD). Donor MDSC infusion only partially ameliorates GvHD lethality, however. In order to improve the potential therapeutic benefit and, ultimately, survival outcomes of MDSC therapy, this disclosure describes an investigation of the fate of MDSC after transfer in the setting of acute GvHD (aGvHD). MDSC transferred to lethally-irradiated recipients of allogeneic donor hematopoietic grafts are exposed to an intense inflammatory environment associated with aGvHD, which can directly undermine the suppressive capacity of the MDSCs. Under GvHD inflammatory conditions, MDSC can lose suppressor function and, therefore, their potential to inhibit GvHD lethality. Even brief in vitro exposure to inflammasome-activating mediators can negate the suppressive potential of cultured murine and human-derived MDSCs. Consistent with a role for the inflammasome, donor MDSCs deficient in the adaptor ASC (Apoptosis-associated speck-like protein containing a CARD) that assembles inflammasome complexes conferred improved survival of mice developing GvHD compared to wild-type donor MDSC. These data suggest the use of MDSC as a therapeutic approach for inhibiting GvHD and other systemic inflammatory conditions can be more effective when combined with approaches that limit in vivo MDSC inflammasome activation, thereby empowering MDSCs to maintain their suppressive potential.

For example, allogeneic hematopoietic cell transplantation (aHCT) is a potentially curative therapy for a variety of hematologic diseases including leukemias and lymphomas. The risk of morbidity and mortality from graft-vs-host disease (GvHD) remains an obstacle to widespread use of allogenic transplantation for many maladies including, for example, malignant and non-malignant lymphohematopoietic disorders. Targeted cellular immunotherapy as an adjunct to aHCT can control GvHD while also reducing side effects associated with conditioning regimens by being highly targeted and internally self-regulating. Myeloid-derived suppressor cells (MDSC), defined broadly as myeloid lineage cells with suppressive capacity, emerge coincident with pathologies such as tumors, trauma and infection. De novo MDSC production from the bone marrow (BM) occurs in response to inflammation and growth factor release (e.g., GM-CSF, G-CSF).

MDSCs can suppress systemic immune pathology via unique mechanisms including local amino acid deprivation, nitric oxide, prostaglandin E2, anti-inflammatory cytokines, reactive oxygen species, as well as promotion of regulatory T cells (Tregs). Bone marrow-derived cultures of MDSCs incubated with interleukin-13 (IL-13) suppress aGvHD via an arginase 1-dependent depletion of L-arginine, which in turn inhibits allogenic T cell responses.

Acute GvHD (aGVHD) is often described as having three phases: transplant conditioning, donor T cell priming, and effector phase tissue apoptosis. The conditioning regimen and the rapid priming of a high frequency of allo-specific donor T cells lead to intense systemic inflammation. Since aGvHD expands donor T cells that have the capacity to attack the recipient, an effective approach to inhibit lethality involves dampening T cell responses early post-transplant, when inflammation is mounting and alloreactive T cells are contributing to organ injury, amplifying the inflammatory response. Thus, for donor MDSC to provide effective therapy, these cells must remain viable and function for a sufficiently long period of time to impede alloreactive T cell priming and expansion.

The inflammasome is a multi-molecular complex that acts as a downstream component of innate immune sensing pathways. Factors associated with inflammasome activation include, for example, gut-associated leakage of bacterial products and danger-associated molecules (DAMPs) from dead and dying cells. For inflammasome activation to occur, initiating signals converge and lead to adaptor protein ASC (Apoptosis-associated speck-like protein containing a CARD)-mediated pro-caspase-1 autocatalytic cleavage, and ultimately cleavage and export of active IL-1β or IL-18. Molecules involved in the different inflammasomes vary depending on the source of activating signals and the upstream molecule that coalesces with ASC. For example, AIM2-like receptor (ALR) family inflammasomes can be initiated by binding cytosolic dsDNA to AIM2 (absent in myeloma 2), while the NLRP3 (NOD-like receptor family, pyrin domain containing 3) inflammasome is activated by microbial and host danger signals, and changes in extracellular ATP content.

This disclosure demonstrates that a single early post-transplant MDSC infusion transiently suppresses but does not eliminate GvHD in a murine model of lethal GvHD. The data establish that the inflammation of GvHD drives MDSCs toward a state of inflammasome activation, which is counterproductive to MDSC suppressive function in GvHD mice. However, genetically altering donor MDSCs to disable inflammasome activation can increase GvHD survival relative to control MDSC therapy. Furthermore, the same pathways are active in human MDSCs. Taken together, this new information can improve the therapeutic application of MDSCs. MDSCs in context of GvHD undergo rapid differentiation to $CD11c^+$ activated phenotype MDSCs were generated from cultured fresh bone marrow (BM) with cytokine growth factors GM-CSF and G-CSF in four days. Activation of cultured MDSCs 24 hours prior to harvest with IL-4 or IL-13 stimulates expression of arginase-1 and promotes functional suppression of T cells both in vitro and in the context of GvHD. To demonstrate that MDSC-IL 13 are effective at prolonging survival in a murine aGvHD model, lethally irradiated BALB/c recipients were given allogeneic C57Bl/6 bone marrow plus CD25-depleted T cells to induce aGvHD, in the presence or absence of MDSC-IL13 cellular therapy at day 0. T cells induce aGvHD resulting in a mean survival time of 24.5 days. However, animals receiving MDSC-IL13 therapy had extended survival to 47.5 days (FIG. 1A). Despite an improved clinical outcome, a majority of treated animals succumbed to GvHD-induced death by day 100, suggesting pathology was reduced or delayed, but not eliminated. To investigate how conditions associated with aGvHD might directly alter MDSC function, bone marrow or bone marrow plus T cell (GvHD conditions) with congenic $CD45.2^+$ MDSC-IL13 s were given to $CD45.1^+$ animals that were then sacrificed at day 5 post-transplant to examine the phenotype and function of recovered MDSCs.

Figure 6:
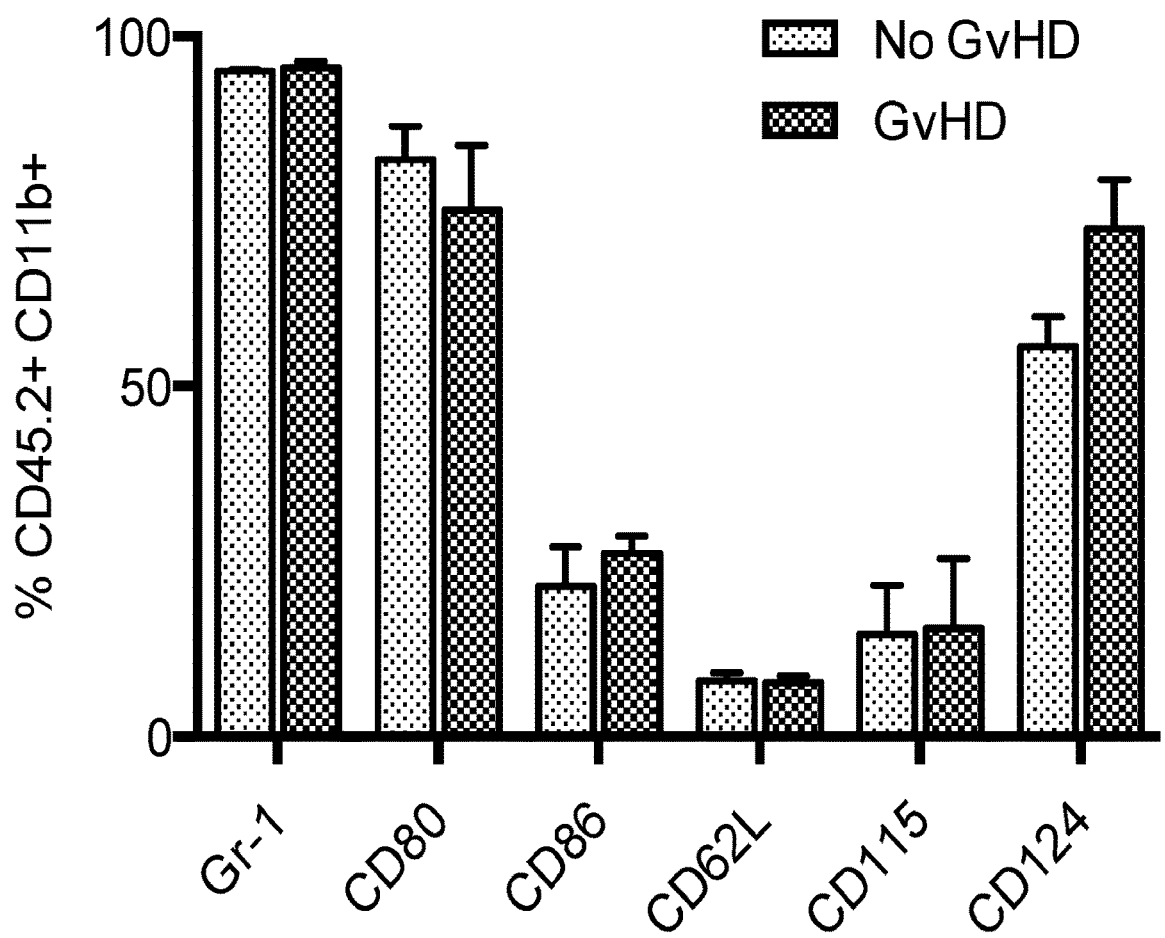
FIG. 6. Extended phenotype of recovered MDSC-IL13. Surface expression of congenic (CD45.2+) MDSC-IL13 recovered from spleens five days after transfer to irradiated animals receiving bone marrow only (no GvHD) or bone marrow plus T cells (GvHD). Data represents three replicates per group with p=ns (>0.05) for all markers shown. Data are representative of two independent experiments.

Phenotypically, MDSCs recovered from transplanted animals receiving only conditioning plus bone marrow maintained an immature $CD11c^{lo}$, $MHCII^{lo}$, $F4/80^{int}$ appearance (FIG. 1B and FIG. 1C). However, MDSC-IL13s transferred to animals undergoing aGvHD conditions ($CD8^+$ $CD4^+$ T cells, CD25-) upregulated CD11c and MHC class II, hallmarks of activated myeloid cells. F4/80 expression was also increased, suggesting activation and differentiation occurred rapidly in response to the ongoing inflammatory environment promoted by allo-reactive T cells (FIG. 1B and FIG. 1C). Other markers of co-stimulation and activation remained unchanged (FIG. 6). To measure the functional status of recovered MDSCs, ex vivo isolated MDSCs were co-cultured with anti-CD3ε mAb-activated, CFSE-labeled T cells. MDSC-IL13s from day 5 animals transplanted with bone marrow only were highly suppressive (FIG. 1D, No GvHD). In contrast, T cell responses in the presence of MDSC-IL13s recovered from GvHD animals showed only a slight reduction in overall proliferation relative to the no MDSC control group (FIG. 1D), indicating a loss of suppressor cell function of MDSCs in GvHD recipients.

One explanation for the loss of suppression by MDSCs in vivo could be compromised survival of the suppressive cells. MDSC viability is maintained by continuous suppression of the extrinsic caspase-8 and intrinsic mitochondrial death pathways. Manipulating either of these pathways can cause a rapid decline in MDSC viability and a concomitant decrease in suppression. The number and viability of transferred cells in recipient spleens post transfer was investigated. No significant differences were observed between bone marrow only and GvHD conditions when looking at total $CD45.2^+$ $CD11b^+$ cell number or viability at day 5 (FIG. 1E). These data suggest that MDSC-IL13s reduce aGvHD for a limited period of time post-transplant and that MDSC-IL13s subsequently lose suppressor function under GvHD conditions, resulting in a failure to sustain a therapeutic benefit.

Multiple MDSC-IL13 Infusions Improve GvHD Long-Term Survival

Figure 8:
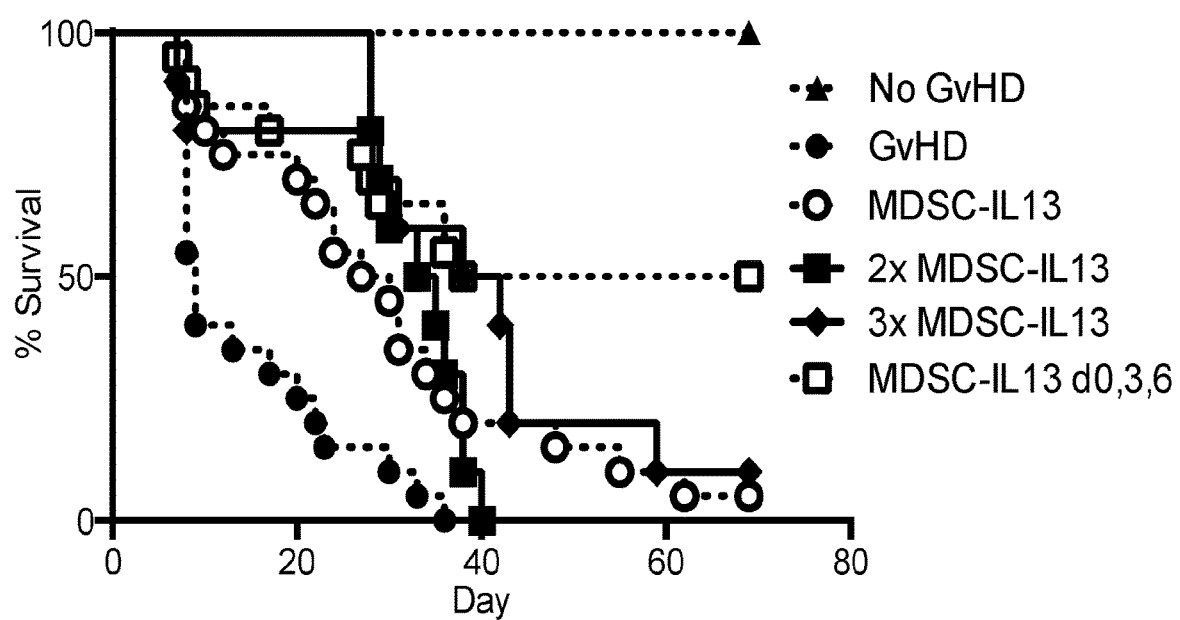
FIG. 8. High dose MDSC-IL13. Kaplan-Meier survival graph showing effect of increased MDSC-IL13 day 0 doses in model of GvHD. In order to distinguish 2× and 3×MDSC treatment groups, data already shown in FIG. 1F is indicated by a dotted line and slightly smaller symbols. Data represents combination of two independent experiments with n=10 per group for 2× and 3× doses. All mice receiving MDSC demonstrated increased survival versus GvHD p<0.001. 1×, 2×, or 3× day 0 doses of MDSC-IL13 are not significantly different from one another.

Increasing the ratio of MDSC-IL13s to T cells during GvHD induction from 3:1 to 6:1 (2×) or 9:1 (3×) at the time of transplant did not significantly increase overall survival (FIG. 8). In contrast, repetitive doses of freshly cultured MDSC-IL13s promoted and/or maintained a suppressive environment during the peri-transplant period of T cell priming during aGvHD. Three infusions of cultured MDSC-IL13s were given on day 0, day 3, and day 6 post-transplant, totaling an aggregate MDSC-T cells ratio of 9:1. Multiple MDSC-IL13 infusions promoted a cohort (50%) of long-term survivors versus <10% long-term survivors when given a single day 0 MDSC-IL13 infusion (FIG. 1F). The observation that repeated infusions of freshly cultured MDSC-IL13s augment survival supports the hypothesis that the intense inflammatory environment found during the induction of aGvHD does not affect MDSC persistence or viability but instead changes the host environment so that transferred MDSC-IL13s are effectively less suppressive with time.

Associated Conversion to IL-1β Production, Inflammasome Activation

Figure 2:
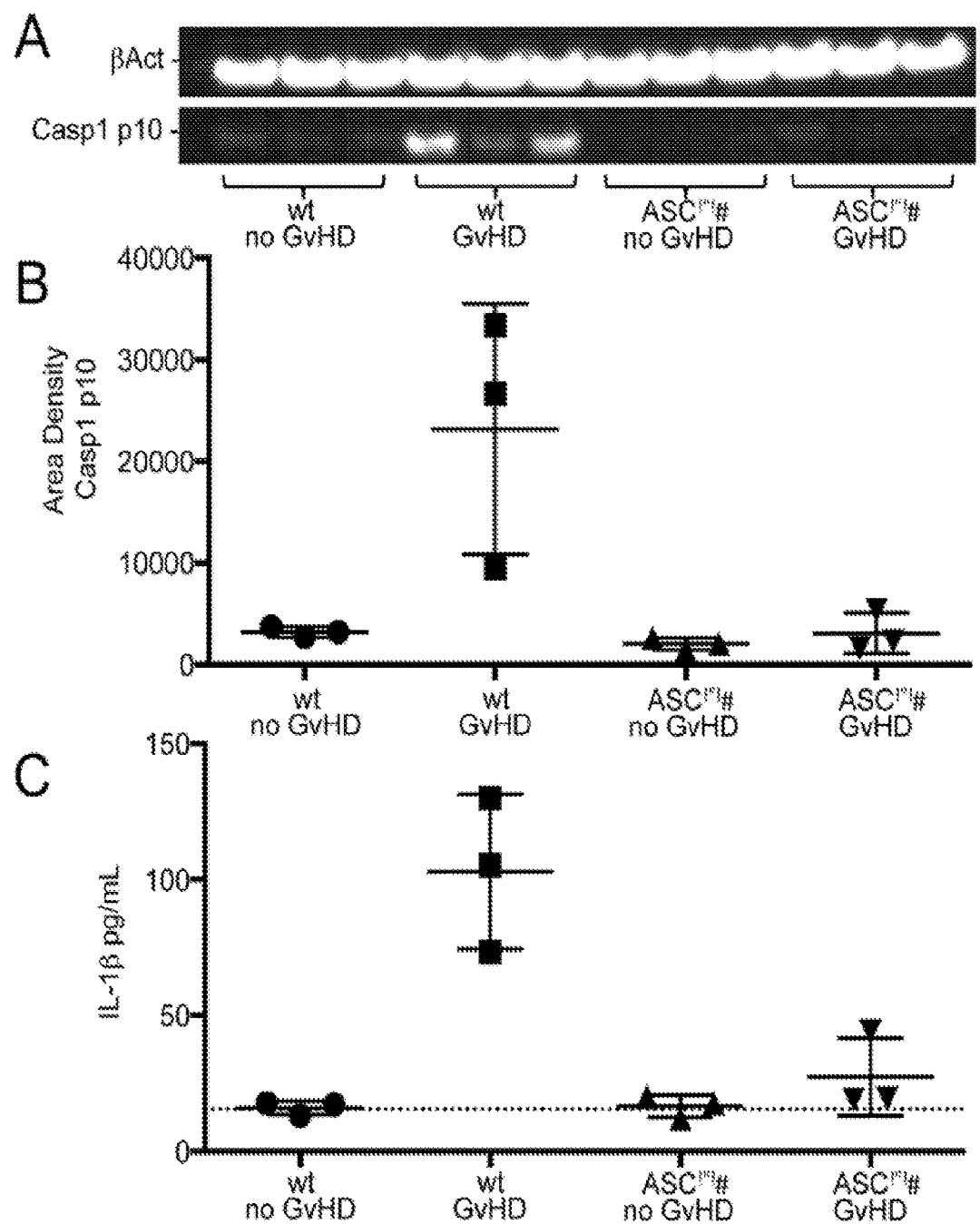
FIG. 2. Inflammasome activity evident in recovered MDSCs. (A) Western blot of cell lysates from recovered wild-type or ASC$^{-/-}$ MDSC-IL13 probed for active p10 form of caspase-1 and (β-actin. ImageJ software was used to convert to grayscale, straighten and crop gel image to highlight lanes of interest according to size. (B) Caspase-1 p10 blot quantification relative to (β-actin, GvHD vs all other groups, p<0.05. Quantification was carried out on scanned blots by densitometric analysis from ImageJ software (NIH) (C) IL-1β ELISA of supernatants after day 5 recovered MDSC-IL13 were plated in complete RPMI media overnight, GvHD vs all other groups, p<0.05. Dotted line indicates limit of ELISA detection. All data are representative of two independent experiments.

Host NLRP3 inflammasome activity can exacerbate GvHD in a murine model. Moreover, GvHD patients can exhibit increased levels of inflammasome-associated serum caspase-1 and IL-1β. Additionally, MDSCs readily produce IL-1β when exposed to certain chemotherapeutic agents, resulting in an altered anti-tumor response. Cell lysates from MDSC-IL13s recovered after five days in GvHD conditions were probed for the processed p10 form of caspase-1, an upstream mediator of inflammasome activity. Western blot analyses showed increased amounts of caspase-1 p10 in MDSC-IL13s recovered from GvHD conditions relative to MDSC-IL13s recovered from bone marrow only transplant control recipients (FIG. 2A and FIG. 2B). Further evidence for MDSC conversion to inflammasome activation was found when recovered MDSC-IL13s were placed in complete media for an overnight culture; analysis of supernatants demonstrated increased IL-1β from GvHD conditions (FIG. 2C). These data establish a correlation between MDSC-IL13 in the context of aGvHD conditions and inflammasome activity.

MDSC-IL13 in vitro Induction of IL-1β Involves ASC

Figure 3:
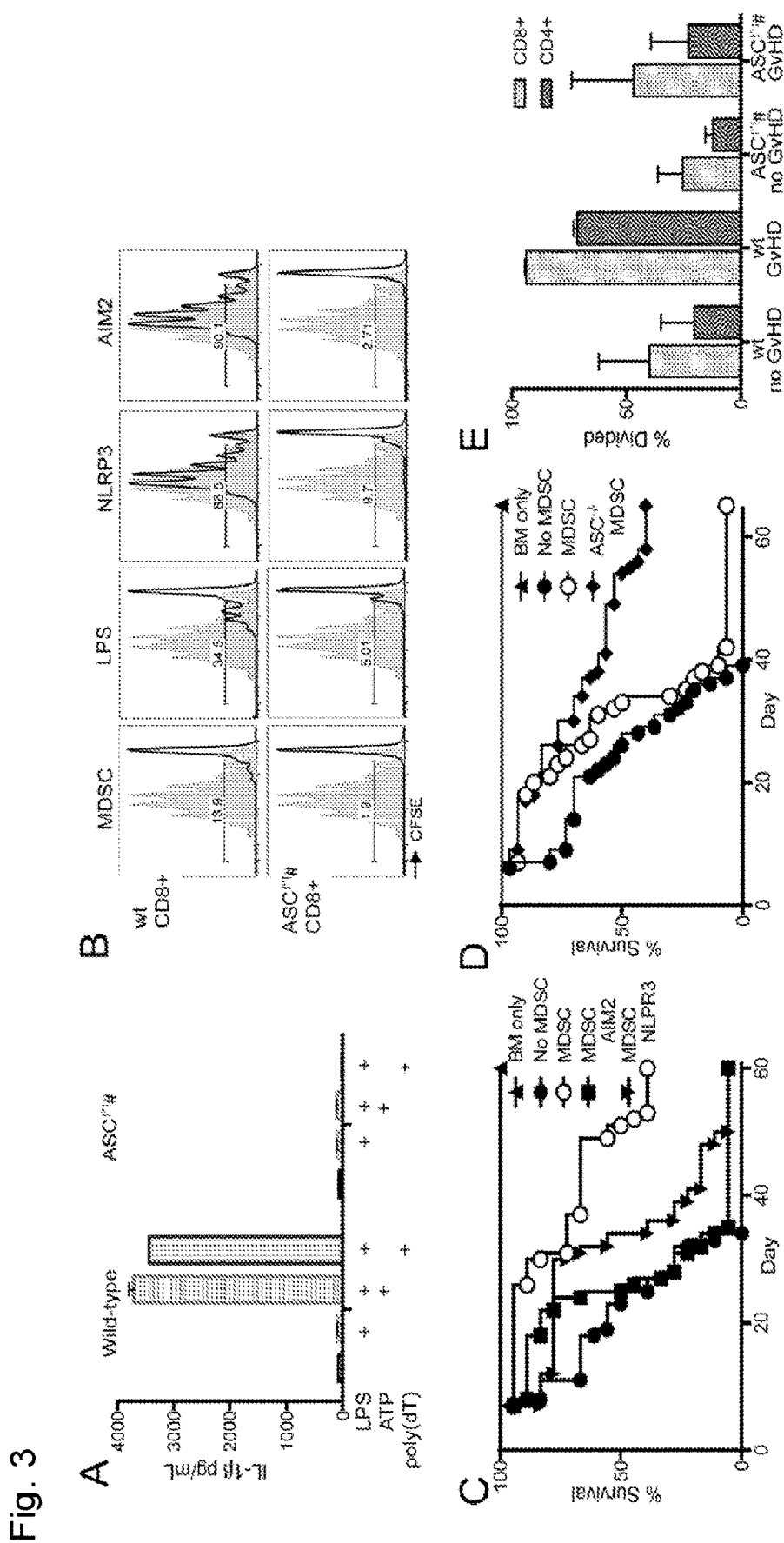
FIG. 3. In vitro inflammasome induction in MDSC leads to loss of suppressor function Inflammasome induction in freshly cultured wild-type and ASC$^{-/-}$ MDSC-IL13 was carried out by adding 0.2 µg/ml LPS for three hours, followed by addition of 2 mM ATP or 0.8 µg/ml poly(dT) transfection. (A) Culture supernatants were harvested after an additional 1 hour and assayed for IL-1β production by ELISA. Data are representative of three independent experiments. (B) Inflammasome induced MDSC-IL13 were washed extensively and plated in a CFSE suppression assay at a 1:1 ratio, data is representative of gated CFSE-labeled CD8$^+$ responder T cells, n=6 samples/group from two independent experiments. NLRP3 indicates LPS+ATP treatment and AIM2 indicates LPS+poly(dT) treatment, gray histogram represents no MDSC proliferation control. Gated CD4$^+$ responder T cells shown in FIG. 10. (C) Kaplan-Meier survival curve of C57B1/6→BALB/c GvHD model using inflammasome induced MDSC-IL13, treated as above. MDSC vs. no MDSC p<0.0001, MDSC vs. MDSC AIM2 p<0.0001, MDSC vs. MDSC NLRP3 p=0.0029. Data represent n=18 animals per group, combined from two independent experiments. (D) Kaplan-Meier survival curve of GvHD using MDSC-IL13 generated from either wild-type or ASC$^{-/-}$ mice as indicated. Data represent n=30 animals per group in three independent experiments. MDSC vs no MDSC p=0.0399, MDSC vs. ASC$^{-/-}$ MDSC p=0.0006. (E) Histograms represent % divided CFSE-labeled responding T cells when plated against recovered wild-type or ASC$^{-/-}$ MDSC-IL13 from day 5 post-transplant at a ratio of 1:1 and harvested on day 3. Significant p values (<0.05) were found when comparing any single group to wild-type MDSC-IL13 recovered from GvHD mice.
Figure 9:
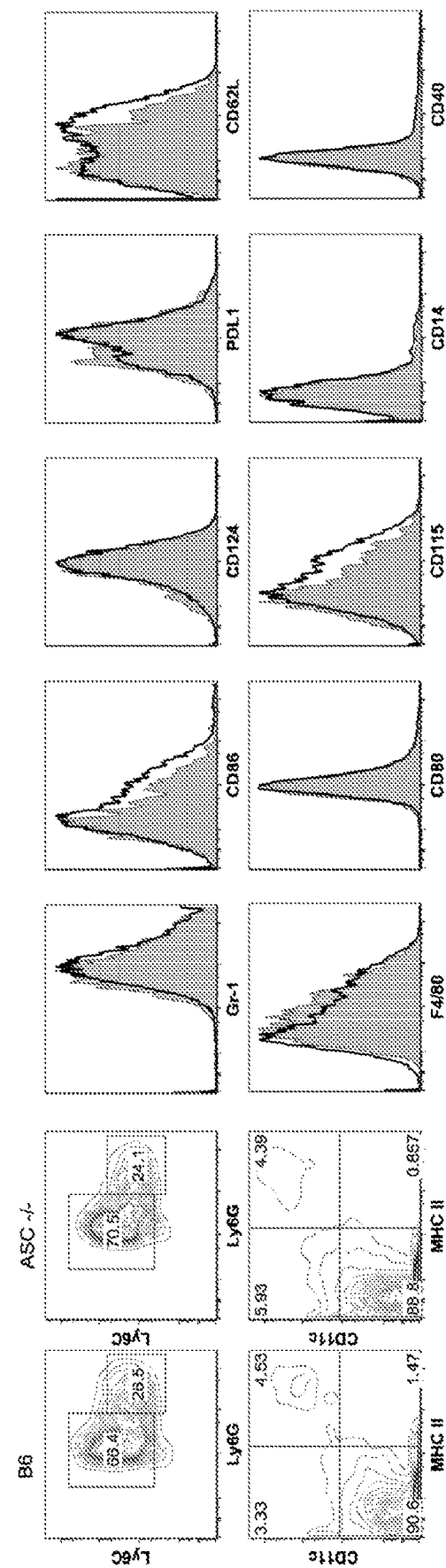
FIG. 9. MDSC-IL13 day 0 infusion phenotype. Surface expression of indicated markers for wild-type B6 (shaded) and ASC ko (bold) MDSC-IL13 on harvest day (day +4 culture) prior to infusion. Data are representative of at least three independent experiments.
Figure 10:
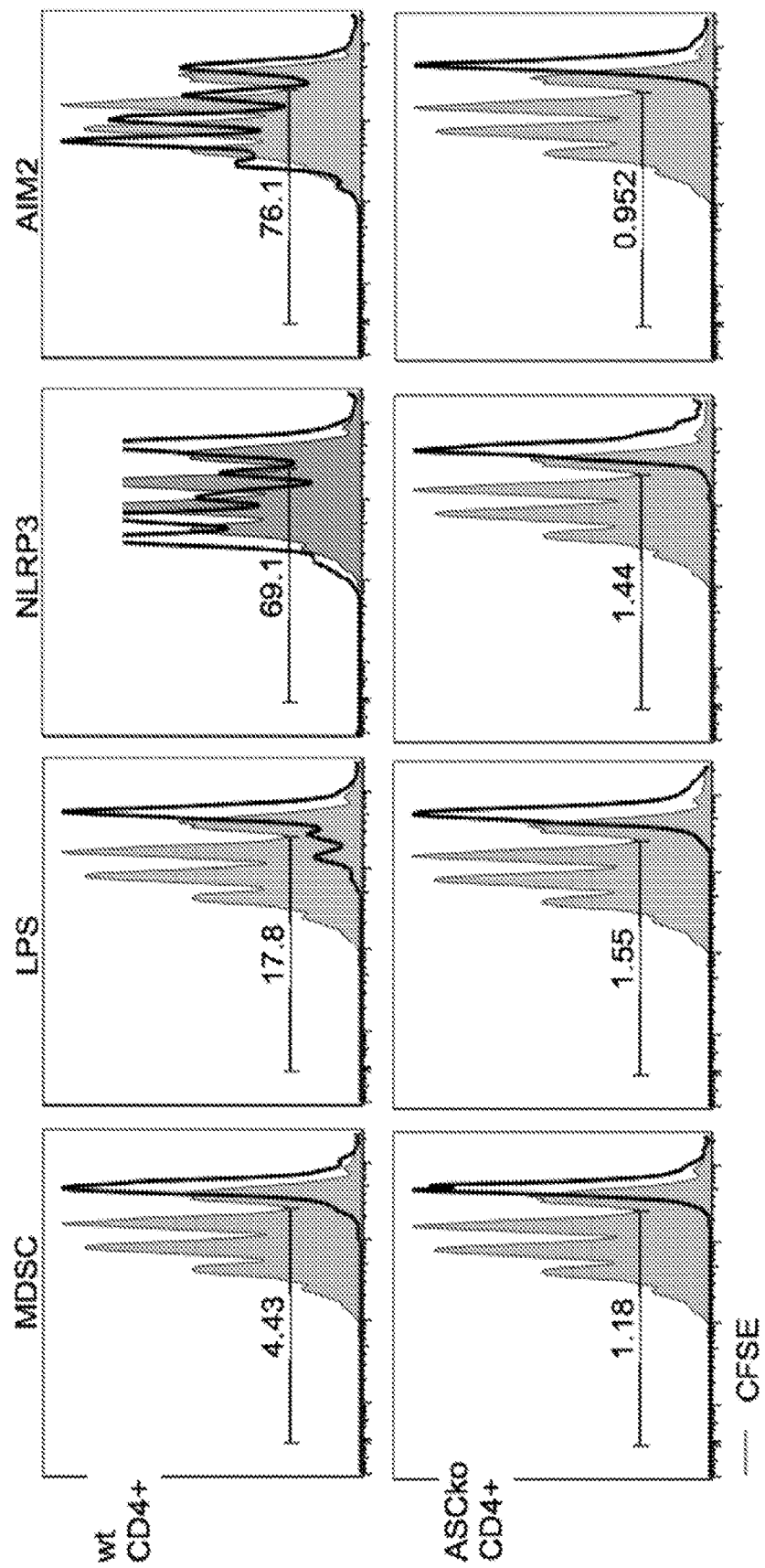
FIG. 10. ASC-dependent inflammasome induced loss of suppression for CD4 responder T cells. As in FIG. 3B, wild-type (wt) or ASC ko MDSC-IL13 were treated as indicated, and washed extensively then applied to a CFSE T cell proliferation assay at a 1:1 ratio. Shown are representative plots of gated CD4+ responder T cells, from two independent experiments.

IL-1β can directly interfere with Treg-mediated suppression and promotion of T effector function. To further investigate a role for inflammasome activation and IL-1β production, in vitro inflammasome induction in cultured MDSC-IL13 was examined. NLRP3 and AIM2 represent two major families of inflammasomes in which a variety of signals can potentiate the inflammasome cascade, but the adaptor protein ASC may be a common component required for full activation of the inflammasome. Wild-type and $ASC^{-/-}$ ($Pycard^{-/-}$) bone marrow were used to generate MDSC-IL13s to test whether they could be induced for inflammasome activity. At the time of transfer, $ASC^{-/-}$ MDSC-IL13s had a similar surface phenotype to wild-type MDSC-IL13s (FIG. 9). The NLRP3 inflammasome was tested by incubating MDSC-IL13s with LPS for three hours followed by ATP, while the AIM2 inflammasome was engaged using LPS followed by poly(dT) transfection. In as little as one hour after the secondary stimulus, IL-1β was detected in culture supernatants from wild-type MDSC-IL13s (FIG. 3A). However, $ASC^{-/-}$ MDSC-IL13s produced no detectable IL-1β, establishing that MDSC-IL13s are capable of rapidly responding to changes in their environment to produce the pro-inflammatory mediator IL-1β in an ASC-dependent fashion. Moreover, inflammasome induction of MDSC-IL13s can alter their suppressive capacity. Following the same procedure to induce inflammasomes in just four hours, MDSC-IL13s were then washed extensively and plated in an in vitro suppression assay of T cell proliferation to anti-CD3ε stimulation. In vitro inflammasome induction reduces the ability of MDSC-IL13s to functionally suppress responding $CD8^+$ (FIG. 3B) and $CD4^+$ (FIG. 10) T cells. Furthermore, this effect was also dependent on ASC, supporting the hypothesis that inflammasome activation is associated with a loss of suppressive function rather than, for example, compromised viability and/or other maturation factors.

Inflammasome Induction Reduces Efficacy of MDSC-IL13 in GvHD

In vitro cultured MDSC-IL13s were treated as above for activation of the NLRP3 or AIM2 inflammasome, followed by extensive washing prior to transfer into the aGvHD model. As seen for in vitro suppression, inflammasome activation of MDSC-IL13s reduced the GvHD survival benefit compared to control MDSC-IL13 therapy, which significantly increased GvHD survival ($p<0.0001$, FIG. 3C).

Since MDSC-IL13 conversion to a mature, inflammasome-activated state after therapeutic transfer is implicated in the setting of aGvHD, using MDSC-IL13s genetically incapable of inflammasome activation may better maintain function and further enhance GvHD survival. Indeed, recipients of $ASC^{-/-}$ MDSC-IL13s had further improved survival relative to wild-type MDSC-IL13s ($p=0.0006$), both of which were significantly better than the no MDSC group (FIG. 3D). Furthermore, $ASC^{-/-}$ MDSC-IL13s recovered from GvHD animals five days post transfer had increased T cell suppressive capacity compared to wild-type MDSC-IL13s (FIG. 3E). These findings together directly implicate MDSC-IL13 intrinsic inflammasome activation under GvHD conditions as playing a role in limiting efficacy of MDSC cellular therapy.

Figure 4:
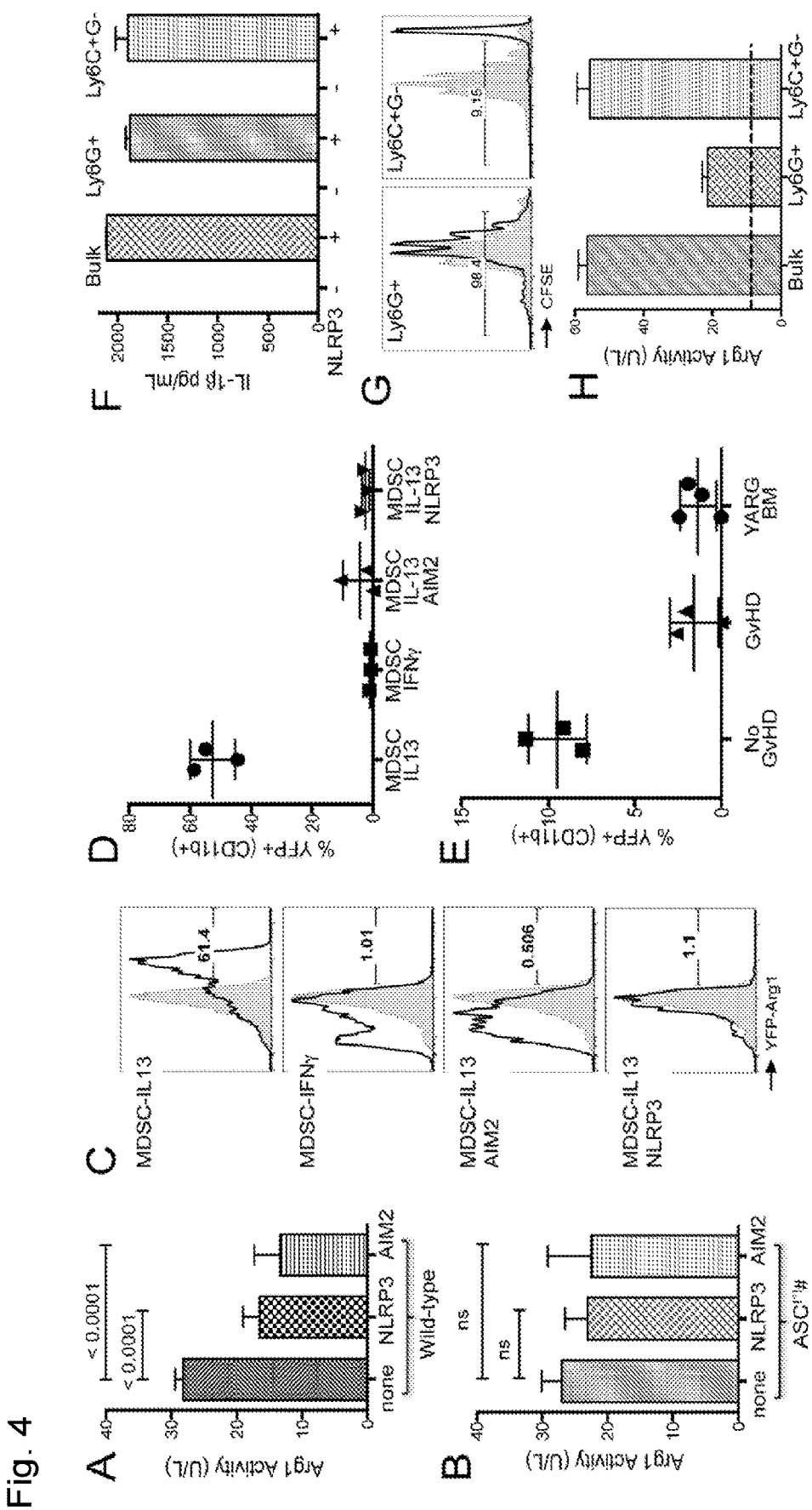
FIG. 4. Inflammasome induction in MDSC associated with loss of Arg1 expression MDSC-IL13 were induced for NLRP3 or AIM2 inflammasomes as indicated, washed extensively and re-plated in complete media overnight. (A) Enzymatic activity of cell-associated Arg1 for wild-type or (B) ASC$^{-/-}$ MDSC, normalized to total cell number. Data are pooled from two independent experiments. MDSC generated from YFP-Arg1 transgenic mice, followed by in vitro induction of inflammasomes and replating in complete media. (C) YFP fluorescence for CD11b-gated MDSC after two additional days in culture indicated as representative histograms (shaded histogram represents unstimulated YARG bone marrow) and (D) summary data of % YFP$^+$. (E) YFP detection for MDSC-IL13 recovered from day 5 transplanted animals with bone marrow only (no GvHD) or bone marrow plus whole T cells (GvHD). YARG bone marrow (YFP-Arg1 bone marrow) indicates baseline YFP fluorescence. (F) IL-1β production before and after NLRP3 (ATP+LPS) inflammasome activation for bulk MDSC-IL13 or sorted granulocytic Ly6G+C+ (Ly6G+) and monocytic Ly6C+ subsets. (G) CFSE proliferation of anti-CD3ε driven CD8+ B6 T cell responses in the presence of sorted granulocytic (Ly6G+) or monocytic (Ly6C+) subsets of MDSC-IL13 at a 1:1 ratio. (H) Cell-associated arginase bioactivity for bulk MDSC-IL13 and sorted granulocytic (Ly6G+) or monocytic (Ly6C+) subsets. The dashed line indicates background activity for Arg1-deficient splenocytes. Data regarding MDSC subsets is representative of 3 independent experiments.
Figure 5:
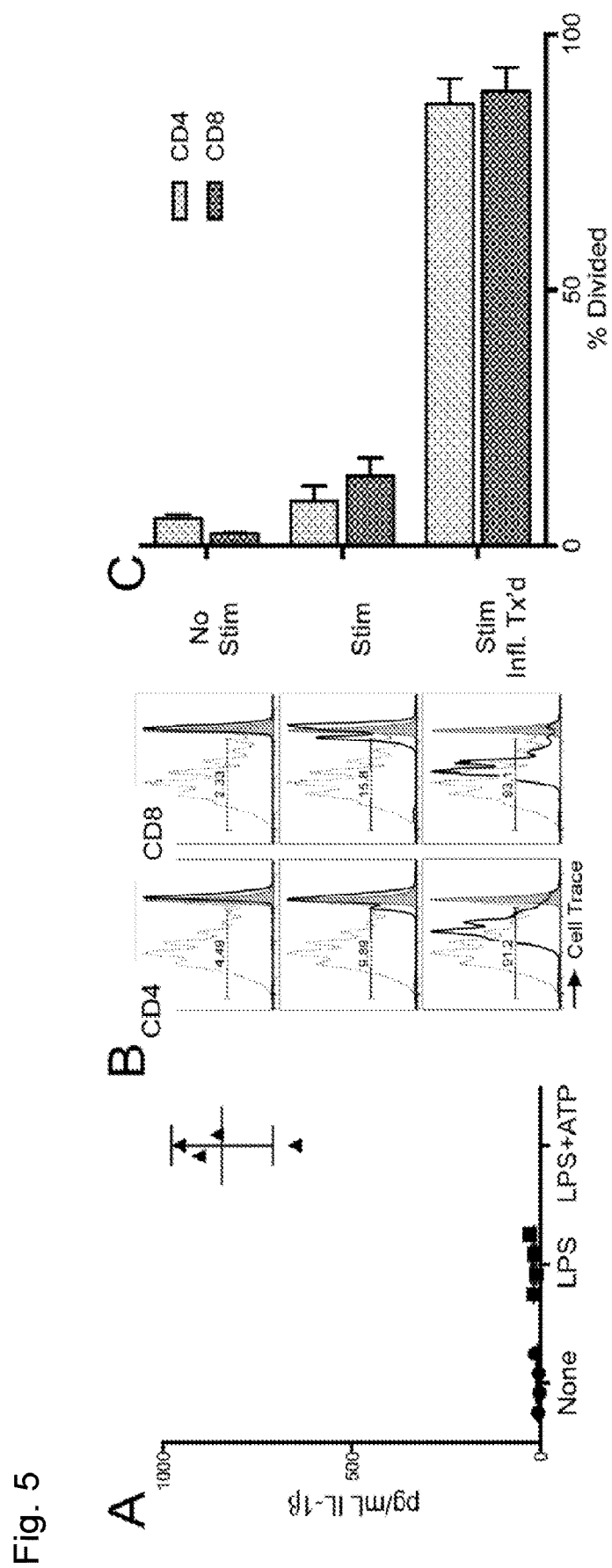
FIG. 5. Inflammasome induction in human MDSC interferes with their suppressor function. Human MDSC were generated from donor PBMC. (A) IL-1β ELISA of supernatants from MDSCs treated for three hours with 0.2 μg/ml LPS for three hours followed by 2 mM ATP for one hour prior to harvest. Data are representative of n=2 experiments. (B) Representative histograms of CellTrace Violet (Life Technologies, Carlsbad, Calif.) labeled responder PBMC in presence of cultured human MDSCs from unrelated donors indicated by solid line. Dotted line indicates no MDSC proliferation control, gray histogram indicates PBMC alone (no CD3ε or MDSC). No Stim represents the allo-response against MDSC with no anti-CD3ε. Stim indicates addition of anti-CD3ε microbeads (2:1)+IL-2 (100 U/ml) to demonstrate MDSC suppression of T cell activation. Stim+Infl. Tx'd indicates MDSC have been treated for inflammasome activation prior to plating with anti-CD3ε microbeads+IL-2. (C) Aggregate data show percent division of responding CD8 and CD4 T cells. Data represent responses from three unrelated PBMC donors, and is representative of two independent experiments.

The mechanism for MDSC-IL13-mediated suppression of GvHD is arginase-1 (arg1) activity that directly undermines T cell responsiveness and promotes GvHD survival. The bioactivity of arg1 enzyme from MDSC-IL13s after inflammasome induction was measured to determine whether arg1 activity was reduced in concert with inflammasome induction. A marked drop in arg1 activity as measured by either mRNA (not shown) or bio-enzymatic activity was found when either NLRP3 or AIM2 inflammasomes were induced (FIG. 4A and FIG. 4B). A similar drop was not evident in $ASC^{-/-}$ MDSCs, though there was a trend, suggesting that the pathways may not be directly linked. To further investigate arg1 activity, YFP-Arg1 transgenic animals (YARG, in which arg1 expression is linked to yellow fluorescence protein (YFP)) were used, allowing one to quickly assay for an associated loss of expression. IL-13 readily upregulates YFP fluorescence, while IFNγ (which induces iNOS-expressing MDSCs) did not increase YFP fluorescence (FIG. 4C and FIG. 4D). As above, inflammasome induction via NLRP3 or AIM2 pathways resulted in a concomitant loss of YFP fluorescence, indicating that arg1 expression had been arrested in association with inflammasome inducing conditions. Finally, MDSC-IL13s generated from YARG transgenic animals were applied to the transplant model, given either bone marrow only or bone marrow plus whole T cells for GvHD conditions. YFP fluorescence from MDSC recovered after five days from bone marrow only animals was reduced relative to expression immediately after culture, but still readily detected above background (FIG. 4E). However, in MDSC-IL13s recovered from GvHD animals, YFP was no longer detectable, being reduced to background levels seen in un-stimulated bone marrow. These results further support a link between a loss of arg1 expression and inflammasome activity during GvHD.

MDSCs are often defined as heterogeneous, with two major subsets described in murine systems being granulocytic (Ly6G$^+$) and monocytic (Ly6C$^+$G$^-$). Each subset was evaluated to determine whether each had a similar capacity for inflammasome activation and how suppressor capacity might be differentially affected. MDSC-IL13s from cultured bone marrow are >90% Ly6C+ (FIG. 9), and were sorted based on Ly6G expression. NLRP3 inflammasome activating conditions lead to equivalent levels of IL1β production for both Ly6C$^+$G$^-$ monocytic and Ly6G$^+$ granulocytic subsets (FIG. 4F). However, when applied to an in vitro suppression assay independent of inflammasome activation, the suppressor capacity was contained virtually in its entirety within the Ly6C$^+$G$^-$ subset (FIG. 4G). Furthermore, arg1 bioactivity was associated with the monocytic subset (FIG. 4H). Together, these data indicate that the loss of suppressor function in GvHD mice was associated with inflammasome activity and not due to a shift toward Ly6G$^+$ or differences in IL1β production capacity. Thus, the relatively higher frequencies of Ly6C$^+$G$^-$ subset in the GvHD versus no GvHD group does not account for the loss of suppressor capacity in vivo.

Human Cultured MDSCs Lose Function when their Inflammasome is Activated.

MDSCs were generated from human peripheral blood mononuclear cells (PBMCs) as previously described (Lechner et al., 2010, *J Immunol* 185(4):2273-2284). These MDSCs were used to investigate whether human MDSCs might have a similar pre-disposition towards inflammasome-activated loss of function as found with murine MDSCs. Human PBMCs, enriched for the myeloid marker CD33, were cultured for seven days with GM-CSF and IL-6. Under these conditions, human MDSCs suppressed anti-CD3ε mAb-driven proliferation of unrelated PBMCs responders. Human MDSCs were confirmed as capable of responding to inflammasome activating conditions, by adding LPS followed by ATP to engage the NLRP3 inflammasome. Both LPS and ATP are needed to drive MDSC production of IL-1β (FIG. 4A). Next, inflammasome-activated MDSC were added to anti-CD3ε mAb-driven PBMC proliferation assay. As in the murine system, MDSCs exposed to inflammasome activating components (Stim+ Infl. Tx'd) lost suppression concomitant with IL-1β production.

Thus, allo-reactive T cells are a contributing factor to morbidity and mortality in clinical GvHD, and the use of regulatory cell therapy can be a viable strategy to control them. MDSCs can be generated from normal bone marrow in a relatively short amount of time and can effectively suppress GvHD, autoimmunity, and allo-graft rejection. This disclosure reports that MDSCs activated by the cytokine IL-13 produce arg1 that, in turn, allows the MDSCs to suppress GvHD. However, in a stringent GvHD model with full MHC mismatching, MDSC therapy promotes extended survival but fails to ultimately protect a majority of animals from lethal GvHD. This disclosure further demonstrates that intrinsic inflammasome activation of adoptively transferred MDSCs limits their efficacy in vivo. Cultured MDSCs are capable of rapidly responding in an ASC-dependent fashion to produce significant amounts of IL-1β, resulting in an associated loss of suppression in vitro. Furthermore, shortly after in vivo transfer, MDSCs in the context of aGvHD convert to a mature CD11c$^+$ phenotype and exhibit a loss of ex vivo suppressive capacity. These MDSCs have increased amounts of caspase-1 p10, an indicator of inflammasome activation, and secrete IL-1β when placed in culture overnight, unlike controls under non-GvHD conditions.

In contrast, when inflammasome activation is genetically prohibited using ASC$^{-/-}$ MDSC-IL 13s, GvHD survival is improved over wild-type MDSC-IL13 transplant recipients and recovered ASC$^{-/-}$ MDSC-IL13s maintain better ex vivo suppressive capacity. Additional methods to alter MDSC susceptibility to inflammasome activation/conversion can include genetic knockdown of ASC or other inflammasome associated genes (e.g., NLRP3, AIM2, Caspase-1). The genetic knockdowns can be obtained using, for example, sh/siRNA, TALEN, meganuclease, megaTALENs, and/or CRISPER technologies, and/or site directed mutagenesis.

Myeloid cells are involved in initiating and shaping immune responses in both pro-inflammatory and anti-inflammatory directions, and demonstrate remarkable plasticity. This adaptability may be both a blessing and a curse, in that it allows one to rapidly generate highly suppressive cells from normal bone marrow in vitro, yet permits the transient efficacy seen upon transfer to a severe inflammatory environment such as aGvHD. While MDSCs are described as heterogeneous in nature and phenotypic markers don't always translate between disease models or species, inflammasome activation pathways appear to be highly conserved. In the data reported in this disclosure, MDSCs generated from mouse bone marrow or human PBMCs readily activate inflammasomes resulting in IL-1β production that correlates to a loss of suppressor function. Patients with aGvHD can exhibit cleaved caspase-1 and increased IL-1β, further supporting the conclusion that GvHD is associated with inflammasome activation. MDSCs are nearly ubiquitously associated with established tumors and can actively perturb immune therapy interventions. One distinction between tumor-induced and GvHD-induced inflammasome activation of MDSCs is that tumor-associated MDSC development occurs in the setting of chronic localized inflammation, in contrast to the intense, systemic inflammatory response of GvHD.

Because GVHD-activated MDSCs secrete IL-1β, it is possible that such MDSCs contributed to the GVHD lethality process. IL-1β has pleiotropic effects dependent on the cell producing it, the state of the surrounding microenvironment, and temporal expression, but is generally understood to be pro-inflammatory and in some instances counter-regulatory. When MDSC-IL13 cells recovered from day +5 GvHD transplant recipients are applied to an in vitro suppression assay, the proportion of T cells proliferating were not different than controls with no MDSCs, although proliferating T cells underwent fewer cell divisions, suggesting some suppressive capacity remained. These data suggest that GVHD-activated MDSC-IL13s did not directly drive GVHD lethality, consistent with the finding that survival curves in MDSC-IL13-treated recipients paralleled those of no MDSC controls, after a 2-3 week delay. Arginase-1 expression, which promotes the survival benefit conferred by MDSC-IL13s during adoptive transfer, was inhibited in inflammasome activated MDSCs, potentially accounting for the loss of suppression by donor MDSCs.

The NLR-family of inflammasome mediators, such as NLRP3, are a candidate for promoting inflammasome conversion under GvHD conditions as both ATP and associated danger signals are found after conditioning and can be involved in enhancing GvHD. NLRP3 inflammasome activation in the context of GvHD has been demonstrated for both radiotherapy and chemotherapy induction protocols, resulting in tissue damage and release of danger-associated molecular patterns (DAMPs). Adoptively transferred MDSCs also can be susceptible to inflammasome induction, and the same mediators may contribute to in vivo activation.

Reagents that selectively target the NLRP3 inflammasome may promote dual purposes of inhibiting inflammasome activation in the host and infused donor MDSCs. For example, MCC950, a small molecule inhibitor, and β-hydroxybutyrate (BHB), a ketone produced under metabolic stress have demonstrated specificity toward suppressed NLPR3 activation and NLRP3-mediated diseases. Alternatively, viral and bacterial products, such as dsDNA also can be potent drivers of both GvHD and of the AIM2-like receptor family of inflammasomes. While GvHD development is not dependent on host MyD88/TRIF pathway activity, the release of dsDNA by dead/dying cells from radiation and GvHD-induced injury may amplify lethality under some conditions.

Taken together, the data reported in this disclosure indicate that the therapeutic potential of donor MDSCs can be increased by reducing the extent to which the inflammatory environment of GvHD inhibits the extent to which MDSCs experience inflammasome activation. Pre-treatment of therapeutic MDSC cellular therapy to specifically inhibit inflammasome activation via genetic alteration (e.g., gene expression knockdown, sh/siRNA/meganuclease, megaTALs, CRISPER) or via pharmacologic inhibition (MCC950/BHB) are methods for intrinsically maintaining MDSC function. Furthermore, pharmacologic treatment or MDSC-specific targeting in vivo to deliver drugs and agents that can regulate inflammasome formation or function or agents that regulate inciting factors in the patient that lead to inflammasome activation of the patient (prior to, during, and/or after transplant) also can reduce inflammasome conversion of MDSC cell therapy with the added benefit of preventing host-derived inflammasome activity, which has been shown to be associated with increased severity of GvHD.

Conversely, in the chronically inflamed setting generally associated with tumor growth, de novo MDSC generation and inflammasome activity are often co-associated. Such MDSC suppression may reduce or eliminate the efficacy of chemotherapy, radiation therapy, surgery, and/or immune therapy with drugs, antibodies/proteins, vaccines, and/or cell therapies. Findings presented here demonstrating that MDSC function is directly compromised via inflammasome activity associated with acute GvHD suggest the degree of inflammation influences MDSC functional support. Thus, anti-tumor therapies such as those listed immediately above that are aimed at tumor eradication may be promoted further by boosting local or systemic inflammasome activation with the intent of removing/disabling tumor-associated MDSC.

The state-of-the-art of the field initially suggested that chronic inflammasome activation would increase MDSC suppressor function. However, our findings in GvHD indicate that high level inflammasome activation reverses MDSC suppressive capabilities. Thus, a novel approach to reversing MDSC suppression in tumors can involve activating MDSCs within the tumor using approaches such as, for example, providing an inciting agent such as, for example, uric acid, ATP, agents that stimulate Toll-like receptors, DNA, RNA, and/or other agents that can upregulate inflammasome function.

Thus, in one aspect, this disclosure describes a method of treating a subject having or at risk of having graft-versus host disease (GvHD). Generally, the method includes administering to the subject a plurality of MDSCs in an amount effective to ameliorate at least one symptom or clinical sign of graft-versus-host disease compared to a suitable control subject.

As used herein, the term "treat" or variations thereof refer to reducing, limiting progression, ameliorating, or resolving, to any extent, the symptoms or clinical signs related to GvHD. A "treatment" may be therapeutic or prophylactic. "Therapeutic" and variations thereof refer to a treatment that ameliorates one or more existing symptoms or clinical signs associated with GvHD. "Prophylactic" and variations thereof refer to a treatment that limits, to any extent, the development and/or appearance of a symptom or clinical sign of GvHD. Generally, a "therapeutic" treatment is initiated after GvHD manifests in a subject, while "prophylactic" treatment is initiated before GvHD manifests in a subject. As used herein, "symptom" refers to any subjective evidence of GvHD, while "sign" or "clinical sign" refers to an objective physical finding relating to GvHD capable of being found by one other than the patient.

Also, the term "at risk" refers to a subject that may or may not actually possess the described risk. Thus, for example, a subject "at risk" for developing GvHD is a subject that possesses one or more indicia of increased risk of having, or developing, GvHD compared to individuals who lack the one or more indicia, regardless of the whether the subject manifests any symptom or clinical sign of having or developing GvHD.

In some embodiments, the method can include repeated administrations of MDSCs to replace MDSCs in previous administrations as the previously-administered MDSCs experience inflammasome activation and become less able to suppress alloreactive T cells. That is, sequentially re-administering MDSCs can replenish a population of MDSCs that lose suppression in an inflammatory environment with new MDSCs that have not yet activated their inflammasome function.

In some embodiments, the therapy can include a minimum of at least two administrations of MDSCs such as, for example, at least three administrations, at least five administrations, at least ten administrations, at least fifteen administrations, at least twenty administrations, at least twenty-five administrations, or at least fifty administrations. In some embodiments, the therapy can include a maximum of no more than fifty administrations of MDSCs such as, for example, no more than forty administrations, no more than thirty administrations, no more than twenty administrations, no more than ten administrations, or no more than five administrations. In some embodiments, the therapy can include a range of administrations having endpoints defined by any minimum number of administrations listed above and any maximum number of administrations listed above that is greater than the minimum number of administrations. Thus, in an exemplary embodiment the therapy can include from three to five administrations of MDSCs.

In some embodiments, sequential administrations of MDSCs can be separated by a minimum interval of at least 24 hours such as, for example, at least two days, at least three days, at least seven days, at least 14 days, at least 30 days, or at least 90 days. In some embodiments, sequential administrations of MDSCs can be separated by a maximum interval of no more than one year, no more than six months, no more than 90 days, no more than 60 days, no more than 30 days, or no more than 14 days. In some embodiments, sequential administrations of MDSCs can be separated by an interval characterized as a range having endpoints defined by any minimum interval between administrations listed above and any maximum interval between administrations listed above that is greater than the minimum interval between administrations. Thus, in an exemplary embodiment the therapy can include MDSCs administered at an interval having a minimum of once per day to a maximum of once every other day.

In some cases, at least a portion of the MDSCs can be treated and/or include a genetic modification that causes the MDSCs to resist inflammasome activation. In some cases, the MDSCs can be pre-treated with, for example, a drug, sh/siRNA, and/or CRISPRs that causes the MDSCs to resist inflammasome activation. An exemplary genetic modification that causes the MDSCs to resist inflammasome activation can include a deficiency in apoptosis-associated speck-like protein containing a CARD (ASC).

A similar effect can be achieved in some embodiments by further treating the subject during and/or after MDSC infusion with an agent that inhibits the inflammasome and thereby reduce the extent to which the infused MDSCs are subjected to inflammasome activation. Exemplary approaches for inhibiting the inflammasome can include agents that directly inhibit the inflammasome. Other approaches can involve using an agent that targets and/or at least partially neutralizes an inflammasome inciting agent. Exemplary inflammasome inciting agents include, for example, uric acid, ATP, an agent that stimulates a Toll-like receptor, DNA, RNA, and/or other agent that can upregulate inflammasome function.

The therapy, whether prophylactic or therapeutic, can be administered for a minimum duration of at least one week such as, for example, at least two weeks, at least one month, at least three months, at least six months, or at least one year. The therapy can be administered for a maximum duration of no more than 20 years such as, for example, no more than 10 years, no more than five years, no more than two years, no more than one year, no more than nine months, no more than six months, no more than three months, no more than two months, no more than one month, or no more than two weeks. The therapy can be administered for a duration characterized as a range having as endpoints any minimum duration listed above and any maximum duration listed above that is greater than the minimum duration. Thus, in an exemplary embodiment the therapy can have a duration of from one week to two weeks.

The MDSCs can be formulated into a pharmaceutical composition that includes a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the MDSCs without causing any undesirable biological effects or interacting in a deleterious manner with any of the other components of the pharmaceutical composition in which it is contained.

The pharmaceutical composition may be formulated in a variety of forms adapted to a preferred route of administration. Thus, a composition can be administered via known routes including, for example, parenteral (e.g., intradermal, transcutaneous, subcutaneous, intramuscular, intravenous, intraperitoneal, etc.) routes of administration.

Thus, MDSCs may be provided in any suitable form including but not limited to a solution, a suspension, an emulsion, or any form of mixture. The composition may be delivered in formulation with any pharmaceutically acceptable excipient, carrier, or vehicle.

A formulation may be conveniently presented in unit dosage form and may be prepared by methods well known in the art of pharmacy. Methods of preparing a composition with a pharmaceutically acceptable carrier include the step of bringing the MDSCs into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of MDSCs administered can vary depending on various factors including, but not limited to, the weight, physical condition, and/or age of the subject, and/or the route of administration. Thus, the absolute amount of MDSCs included in a given unit dosage form can vary widely, and depends upon factors such as the species, age, weight and physical condition of the subject, and/or the method of administration. Accordingly, it is not practical to set forth generally the amount that constitutes an amount of MDSCs effective for all possible applications. Those of ordinary skill in the art, however, can readily determine the appropriate amount with due consideration of such factors.

In some embodiments, a single administration of MDSCs can include a minimum of at least $10^5$ MDSCs such as, for example, at least $10^6$ MDSCs, at least $10^7$ MDSCs, at least $10^8$ MDSCs, at least $10^9$ MDSCs, at least $10^{10}$ MDSCs, at least $10^{11}$ MDSCs, or at least $10^{12}$ MDSCs. In some embodiments, a single administration of MDSCs can include a maximum of no more than $10^{13}$ MDSCs such as, for example, no more than $10^{12}$ MDSCs, no more than $10^{11}$ MDSCs, no more than $10^{10}$ MDSCs, no more than $10^9$ MDSCs, no more than $10^8$ MDSCs, no more than $10^7$ MDSCs, or no more than $10^6$ MDSCs. In some embodiments, a single administration of MDSCs can include a number of MDSCs characterized as a range having endpoints defined by any minimum number of MDSCs listed above and any maximum number of MDSCs listed above that is greater than the minimum number of MDSCs. Thus, in one exemplary embodiment, a single administration of MDSCs can include a range of $10^7$ MDSCs to $10^{10}$ MDSCs. In another exemplary embodiment, a single administration of MDSCs can include a range of $4 \times 10^7$ MDSCs to $5 \times 10^8$ MDSCs.

In another aspect, this disclosure describes a method of treating a tumor. Generally, the method includes increasing inflammasome activation of MDSCs sufficiently to disable the suppressor function of the MDSCs in the vicinity of the tumor. In some cases, increasing inflammasome activation can include providing at least one inflammasome inciting agent such as, for example, uric acid, ATP, an agent that stimulates a Toll-like receptor, DNA, RNA, and/or other agent that can upregulate inflammasome function.

The inflammasome inciting agent can be co-administered with a conventional anti-tumor therapy designed to eradicate the tumor such as, for example, chemotherapy, radiation therapy, surgery, and/or immune therapy with drugs, antibodies/proteins, vaccines, and/or cell therapies. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another.

In some cases, the anti-tumor therapy may be administered at the same dose and frequency for which the therapy has received regulatory approval. In other cases, the anti-tumor therapy may be administered at the same dose and frequency at which it is being evaluated in clinical or preclinical studies. One can alter the dosages and/or frequency as needed to achieve a desired level of anti-tumor effect when co-administered with the inflammasome inciting agent. Thus, one can use standard/known dosing regimens and/or customize dosing as needed.

Similarly, the inflammasome inciting agent may be formulated in any suitable form. Moreover, For example, the inflammasome inciting agent may be administered at the same dose and frequency for which it may have received regulatory approval. In other cases, the inflammasome inciting agent may be administered at the same dose and frequency at which it may be being evaluated in clinical or preclinical studies. One can alter the dosages and/or frequency as needed to achieve a desired level of the inflammasome inciting agent. Thus, one can use standard/known dosing regimens and/or customize dosing as needed.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Mice 6-8 wk-old female BALB/c ($H2^d$), C57BL/6NCr ($H2^b$) and B6-Ly5.2/Cr (B6-CD45.1$^+$, $H2^b$) mice were purchased from the National Cancer Institute. ASC knockout mice (Mariathasan et al., 2004. Nature 430 (6996):213-218) and YFP-Arg1 (YARG) mice (Reese et al., 2007. Nature 447 (7140):92-96) on a C57Bl/6 genetic background have been previously described. All mice were bred and housed in a specific pathogen-free facility in micro-isolator cages in protocols approved by the Institutional Animal Care and Use Committee at the University of Minnesota.

MDSC Generation

Murine MDSC were generated by culturing C57Bl/6 bone marrow at $3 \times 10^5$ cells/mL in Dulbecco modified Eagle medium plus 10% fetal calf serum, 50 µM 2-mercaptoethanal, 10 mM HEPES, 1 mM sodium pyruvate, 100 U/mL penicillin, 100 mg/mL streptomycin, and supplemental amino acids (1.5 of each of mM L-glutamine, L-arginine, and L-asparagine). 100 ng/mL granulocyte colony-stimulating factor (G-CSF/Neupogen, Amgen Inc., Thousand Oaks, Calif.) and 2.5 ng/mL mouse granulocyte-macrophage colony-stimulating factor (GM-CSF, R&D Systems, Inc., Minneapolis, Minn.) was added and cultures were incubated at 37° C., 10% $CO_2$ for four days. On day 3, 40 ng/mL recombinant murine IL-13 (R&D Systems, Inc., Minneapolis, Minn.) was added for arginase-1 induction; alternatively IFNγ was added at the same concentration. MDSC were harvested on day 4 by gently removing 70% of the culture supernatant. The remaining media and loosely adherent cells were then collected prior to addition of Trypsin/EDTA. After 10 minutes at 37° C., plates were lightly scraped and washed to collect remaining cells, which when pooled with lightly adherent cells resulting in >92% CD11b$^+$ recovery. For inflammasome induction, on day 4 LPS (0.2 µg/ml) was added to cultures. After three hours, to stimulate the NLRP3 inflammasome 2 mM ATP was added for one hour, alternatively for AIM2 inflammasome activation poly(dT) was added using Lipofectamine 2000 reagent per the manufacturer's instructions (Invitrogen Corp., Carlsbad, Calif.) for one hour prior to washing and analysis of supernatants or adoptive transfer.

Human MDSC were generated from normal donor PBMC, isolated from adult blood obtained from Memorial Blood Center (Minneapolis, Minn.) by centrifugation using a Histopaque gradient (Sigma-Aldrich, St. Louis, Mo.). In vitro generation was carried out as previously described (Lechner et al., 2010. J Immunol 185(4):2273-2284), modified by prior CD33$^+$ myeloid enrichment, which was carried out using Miltenyi MACs system according to instructions. Cultures were harvested on day 7 for inflammasome induction, followed by washing and plating in suppression assays as previously described (Hippen et al., 2008. Blood 112(7): 2847-2857). Human blood bank samples were obtained via guidelines approved by the Committee on the Use of Human Subjects in Research at the University of Minnesota.

GvHD

BALB/c recipients were lethally irradiated using 700cGy total body irradiation one day prior to infusion of $1 \times 10^7$ C57Bl/6 donor bone marrow, $2 \times 10^6$ lymph node purified C57Bl/6 CD25-depleted T cells, and $6 \times 10^6$ cultured C57Bl/6 MDSC-IL13 on day 0 or as indicated. T cell enrichment was carried out using a negative cell isolation system (EASYSEP, Stemcell Technologies Inc., Vancouver, Canada) and biotinylated antibodies to CD19, B220, CD11b, CD11c, NK1.1, γδ TCR and CD25 according to the manufacturer's instructions. Mice were monitored daily for survival.

MDSC Ex Vivo Recovery

Figure 7:
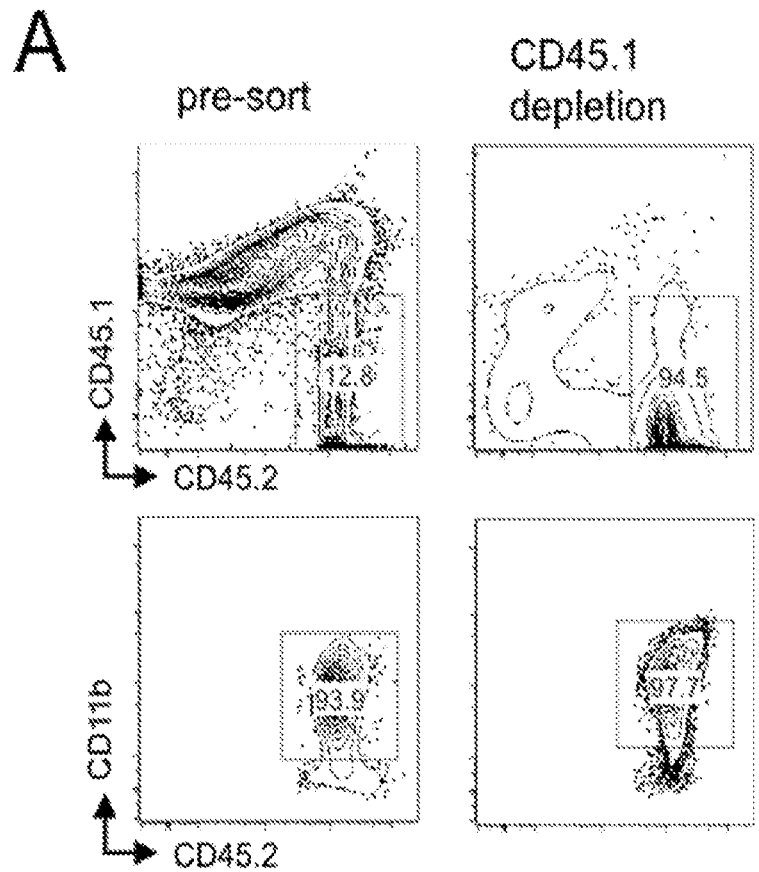
FIG. 7. CD45.2+ MDSC-IL13 recovery. (A) Representative flow plot showing CD45.2+ frequencies of pooled splenocytes before and after enrichment. Bottom graphs represent gated cells indicated in top graph (CD45.2+ CD45.1-ve) (B) Enrichment efficacy of MDSC-IL13 (CD45.2+) from No GvHD and GvHD groups. Data are representative of three independent experiments, n=3 per group.
Figure 7:
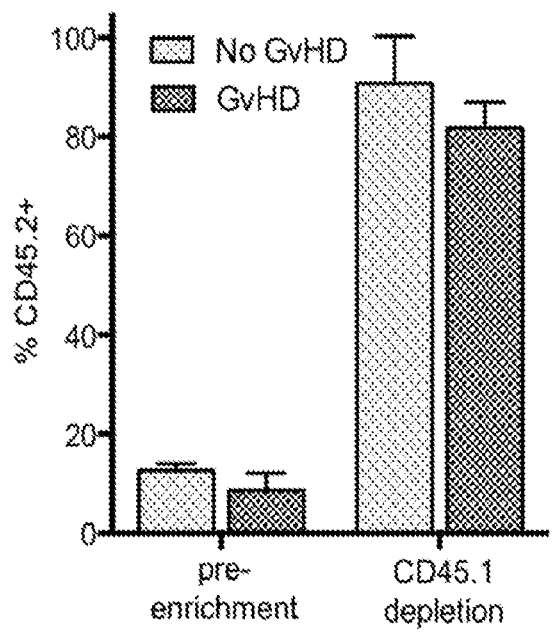

MDSC-IL13 generated from CD45.2+ (B6 or ASC ko) congenic donors were transferred to CD45.1+ recipients as described. Five days post-transplant, spleens from 3-4 recipients were pooled per sample, (n=3 samples per group) in order to increase the recovery and facilitate functional assays. CD45.2+ (MDSC-IL13) splenocytes were isolated by depletion of host and donor T cells using the RAPID-SPHERE EASYSEP method (Stemcell Technologies Inc., Vancouver, Canada) and anti-CD45.1-biotinylated antibody according to the manufacturer's instructions, resulting in >80% CD45.2+ MDSC-IL13 recovery (FIG. 7).

MDSC-IL13 Sorting of Granulocytic (Ly6G+) and Monocytic (Ly6C+ G-ve) Subsets

MDSC-IL13 cultures were bulk labeled with APC-conjugated anti-Ly6G (clone 1A8) antibodies, followed by anti-APC microbead labeling and application to Miltenyi MACs LS columns for separation based on Ly6G+ expression according to manufacturer instructions. This resulted in effective sorting of granulocytic and monocytic subsets that were then used for further analysis.

Flow Cytometry and Suppression Assay

Flow cytometric data acquisition was carried out on a BD LSRFortessa and analysis was done using FlowJo software (FlowJo, LLC, Ashland. Oreg.). For murine suppression assays, responding T cells were stained with 3.5 μM carboxyfluorescein succinimidyl ester (CFSE) and incubated with 0.25 μg/ml anti-CD3ε before analysis on day 3. In human MDSC suppression assays, responder PBMCs were labeled with CELLTRACE Violet (ThermoFisher Scientific, Waltham, Mass.) and stimulated with anti-CDR3ε mAb-coated beads (DYNAL, Thermo Fisher Scientific, Waltham, Mass.; 2:1 ratio) plus 100 U/ml huIL-2; samples were collected on day 4.

ELISA, western blot, and Arginase Assay

Murine and human IL-1β in culture supernatants was assessed using respective BD OptEIA ELISA sets, following manufacturer's instructions (BD Biosciences, San Jose, Calif.). For western blots, purified MDSC were washed and resuspended in lysis buffer containing RIPA, protease (Santa Cruz Biotechnology, Inc., Dallas, Tex.) and phosphatase (Sigma-Aldrich, St, Louis, Mo.) inhibitor cocktail then snap frozen. 4 μg of protein from cell lysates were fractionated in 4-12% SDS-PAGE gels (Invitrogen Corp., Carlsbad, Calif.), transferred on polyvinylidene fluoride (PVDF) membranes (GE Healthcare Co., Little Chalfont, United Kingdom), and probed for detection of cleaved caspase-1 using anti-cleaved caspase-1 p10 rabbit mAb (sc-514, Santa Cruz Biotechnology, Inc., Dallas, Tex.; 1:500). Secondary antibodies used were HRP-conjugated anti-rabbit antibody (Cell Signaling Technology, Inc., Danvers, Mass.) for detection of the anti-cleaved caspase-1 antibodies (1:10,000) and HRP conjugated anti-mouse antibody for detection of the anti-β-actin Ab (1:2750). ImageJ software (National Institutes of Health, Bethesda, Md.) was used to estimate relative quantifications of western blot bands. Arginase-1 activity was determined using QuantiChrom Arginase Assay Kit (Bioassay Systems LLC, Hayward, Calif.). Samples were normalized to 4×10$^5$ cells per sample, washed, pelleted and resuspended in 100 μl of protease inhibitor-containing lyse buffer then assayed according to manufacturer instructions.

Statistical Analysis

Survival studies are represented by Kaplan-Meier survival curves, with statistical comparisons determined using log-rank statistics. The Student's t-test was used for statistical analysis of in vitro acquired data (Prism software, GraphPad Software, Inc., LaJolla, Calif.). $p<0.05$ was defined as statistically significant.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of treating a subject having or at risk of having graft-versus-host disease (GvHD), wherein said method comprises administering to the subject a plurality of myeloid-derived suppressor cells (MDSCs), wherein said MDSCs lack expression of apoptosis-associated speck-like protein containing a CARD (ASC) polypeptides, and wherein said MDSCs comprise a genetic deletion of nucleic acid encoding said ASC polypeptides.

2. The method of claim 1, wherein administering the plurality of MDSCs comprises a plurality of serial administrations of said MDSCs.

3. The method of claim 2, wherein at least one administration of MDSCs occurs at least three days after a previous administration of MDSCs.

4. The method of claim 3, wherein said method comprises at least three administrations of MDSCs.

5. The method of claim 2, wherein said method comprises at least three administrations of MDSCs.

6. The method of claim 1, wherein the GvHD comprises acute graft-versus-host disease.

7. The method of claim 1, wherein said subject is in need of an allogeneic transplantation for lymphohematopoietic disorders.

8. The method of claim 1, wherein said subject is in need of an MDSC therapy.

9. The method of claim 1, wherein said subject is in need of a conditioning regimen.

10. The method of claim 1, wherein said MDSCs comprise the ability to suppress a systemic immune pathology within said subject.

11. The method of claim 1, wherein said MDSCs comprise the ability to impede alloreactive T cell priming and expansion within said subject.

12. The method of claim 1, wherein said MDSCs comprise the ability to inhibit an inflammatory response within said subject.

13. The method of claim 1, wherein said MDSCs comprise the ability to disable inflammasome activation within said subject.

14. The method of claim 1, wherein said MDSCs comprise the ability to reduce risk of having GvHD within said subject.

15. The method of claim 1, wherein said MDSCs comprise the ability to improve GvHD long-term survival of said subject.

16. A method of treating a subject having or at risk of having graft-versus-host disease (GvHD), wherein said method comprises administering to the subject a plurality of myeloid-derived suppressor cells (MDSCs), and
administering to the subject an agent that inhibits the inflammasome in an amount effective to reduce the extent to which the MDSCs are subjected to inflammasome activation, wherein said agent is MCC950 or β-hydroxybutyrate.

17. The method of claim 16, wherein administering the plurality of MDSCs comprises a plurality of serial administrations of said MDSCs.

18. The method of claim 17, wherein at least one administration of MDSCs occurs at least three days after a previous administration of MDSCs.

19. The method of claim 17, wherein said method comprises at least three administrations of MDSCs.

20. The method of claim 18, wherein said method comprises at least three administrations of MDSCs.

21. The method of claim 16, wherein said GvHD comprises acute graft-versus-host disease.

22. The method of claim 16, wherein said subject is in need of an allogeneic transplantation for lymphohematopoietic disorders.

23. The method of claim 16, wherein said subject is in need of an MDSC therapy.

24. The method of claim 16, wherein said subject is in need of a conditioning regimen.

25. The method of claim 16, wherein said MDSCs comprise the ability to suppress a systemic immune pathology within said subject.

26. The method of claim 16, wherein said MDSCs comprise the ability to impede alloreactive T cell priming and expansion within said subject.

27. The method of claim 16, wherein said MDSCs comprise the ability to inhibit an inflammatory response within said subject.

28. The method of claim 16, wherein said MDSCs comprise the ability to disable inflammasome activation within said subject.

29. The method of claim 16, wherein said MDSCs comprise the ability to reduce risk of having GvHD within said subject.

30. The method of claim 16, wherein said MDSCs comprise the ability to improve GvHD long-term survival of said subject.

* * * * *

UNITED STATES PATENT AND TRADEMARK OFFICE
CERTIFICATE OF CORRECTION

PATENT NO. : 10,894,061 B2
APPLICATION NO. : 15/747902
DATED : January 19, 2021
INVENTOR(S) : Blazar et al.

It is certified that error appears in the above-identified patent and that said Letters Patent is hereby corrected as shown below:

On the Title Page

Item (71), Line 5, delete "Albert-Ludwig Universität" and insert -- Albert-Ludwig-Universität --;

Item (56), Line 3, delete "Einsten" and insert -- Einstein --;

In the Claims

Column 19, Lines 16-17, Claim 13, delete "comprise the ability to disable" and insert -- are resistant to --;

Column 20, Lines 27-28, Claim 28, delete "comprise the ability to disable" and insert -- are resistant to --.

Signed and Sealed this
Third Day of May, 2022

Katherine Kelly Vidal
*Director of the United States Patent and Trademark Office*